United States Patent
Ohkoshi et al.

(10) Patent No.: US 6,620,966 B2
(45) Date of Patent: Sep. 16, 2003

(54) PROCESS FOR PRODUCING AROMATIC CARBOXYLIC ACID

(75) Inventors: Fumio Ohkoshi, Okayama (JP); Ikuo Tsuboi, Okayama (JP); Nirou Hoshishima, Okayama (JP)

(73) Assignees: Mitsubishi Gas Chemical Company, Inc., Tokyo (JP); Toyo Boseki Kabushiki Kaisha, Osaka (JP); Mizushima Aroma Company, Ltd., Kurashiki (JP)

( * ) Notice: Subject to any disclaimer, the term of this patent is extended or adjusted under 35 U.S.C. 154(b) by 0 days.

(21) Appl. No.: 10/046,248

(22) Filed: Jan. 16, 2002

(65) Prior Publication Data

US 2002/0099240 A1 Jul. 25, 2002

(30) Foreign Application Priority Data

Jan. 22, 2001 (JP) ........................................ 2001-013243

(51) Int. Cl.[7] .................... C07C 51/16; C07C 51/255
(52) U.S. Cl. .................... 562/412; 562/414; 562/416
(58) Field of Search ................. 562/412, 414, 562/416

(56) References Cited

U.S. PATENT DOCUMENTS 5,723,656 A * 3/1998 Abrams et al. ............. 562/412

FOREIGN PATENT DOCUMENTS

| EP | 0461855 | 12/1991 |
|----|---------|---------|
| EP | 0618186 | 10/1994 |
| EP | 0962442 | 12/1999 |

OTHER PUBLICATIONS

Patent Abstracts of Japan; Publication No.: 08–089706; Publication Date: Apr. 9, 1996; Operation Method of Crystallizer.
Patent Abstracts of Japan; Publication No.: 2000–179831; Publication Date: Jun. 27, 2000; Exhaust Gas Tube Cleaning Device for Ash Melting Furnace.
European Search Report completed Apr. 26, 2002.

* cited by examiner

Primary Examiner—John M. Ford
Assistant Examiner—Zachary C. Tucker
(74) Attorney, Agent, or Firm—Antonelli, Terry, Stout & Kraus, LLP

(57) ABSTRACT

There is disclosed a process for continuously producing an aromatic carboxylic acid comprising the steps of (A) subjecting a poly-alkyl aromatic hydrocarbon to a liquid-phase oxidation by continuously supplying an oxidation reactor with said hydrocarbon, a catalyst, a reaction accelerator, acetic acid containing water and a gas containing molecular oxygen; (B) continuously taking out from the oxidation reactor, the reaction products containing aromatic carboxylic acids, and separating the same into crude aromatic carboxylic acids and acetic acid containing water; and (C) continuously taking out from the oxidation reactor, the oxidative reaction exhaust gas containing evaporated acetic acid containing water, introducing the above gas in a condenser, and condensing the above evaporated acid, wherein acetic acid containing water is supplied to an oxidative reaction exhaust gas inlet line leading to the condenser. The process enables to almost perfectly eliminate the occurrence of troubles in the condenser which is caused by solid matters accompanying the oxidative reaction exhaust gas, and to proceed with stable operation of aromatic carboxylic acid production equipment.

14 Claims, 1 Drawing Sheet

PROCESS FOR PRODUCING AROMATIC CARBOXYLIC ACID

BACKGROUND OF THE INVENTION

1. Field of the Invention

The present invention relates to a process for continuously producing an aromatic carboxylic acid by an oxidation of a poly-alkyl aromatic hydrocarbon in the presence of a catalyst and a reaction accelerator. More particularly, the present invention pertains to the foregoing process which comprises preventing the performance of a condenser from being inhibited by the adhesion to the condenser, of slight amounts of a reaction product and/or a catalytic component that are splashed by accompanying an oxidative reaction exhaust gas which is continuously withdrawn from an oxidation reactor.

2. Description of the Related Arts

An aromatic carboxylic acid is produced by a liquid-phase oxidation of a poly-alkyl aromatic hydrocarbon through an exothermic reaction which is put into practice in a tank type reactor usually equipped with an agitator. In the oxidation process, an oxidation reactor is continuously charged with a poly-alkyl aromatic hydrocarbon, catalytic and components acetic acid containing water as a solvent which is freshly fed or recirculatingly used, each in individual form or as a mixture. The reactor is further charged with a gas containing molecular oxygen at the bottom or in the vicinity thereof.

The aromatic carboxylic acid thus produced is continuously taken out in the form of a slurry solution through a reaction product takeoff port on account of its generally low solubility in acetic acid containing water. After additional oxidative reaction to be conducted at need, the resultant aromatic carboxylic acid is crystallized and separated in one or two or more crystallizers that are connected in series, and is sent to a drying step to be made into the objective product.

The mother liquor separated from the aromatic carboxylic acid, which contains acetic acid containing water as the solvent and soluble catalytic components, is taken out in part to the outside of the reaction system, but the remainder is circulated through the oxidation reactor for reutilization.

The oxidative reaction exhaust gas usually contains at most approximately 8% by volume of oxygen and a small amount of oxidative reaction byproducts each having a low boiling point, and is continuously exhausted through a takeoff port located at the top of the reactor or in the vicinity thereof, while the heat of oxidative reaction is removed by the evaporation of the acetic acid containing water as the solvent, and the evaporated acetic acid containing water accompanies the oxidative reaction exhaust gas, and is exhausted therewith.

The oxidative reaction exhaust gas which contains the evaporated acetic acid containing water is condensed by being passed through one or two or more condensers, and is separated into acetic acid containing water and oxidative reaction exhaust gas composed of non-condensable components. The resultant oxidative reaction exhaust gas is exhausted to the outside of the reaction system directly or at need, through an valuable component recovery step and/or an energy recovery step.

Part of the acetic acid containing water thus separated is sent to a dehydration step, where the water formed by the oxidative reaction is removed, while the dehydrated acetic acid is reused as a solvent for oxidative reaction. The remainder of the acetic acid containing water thus separated is directly returned to the reactor, where it is reused as a solvent for oxidative reaction.

A gas containing molecular oxygen is continuously supplied to the bottom or in the vicinity thereof of the oxidation reactor, where the gas rises through the liquid therein, causing vigorous stirring so as to proceed with the oxidative reaction of a poly-alkyl aromatic hydrocarbon.

The oxidation process for a poly-alkyl aromatic hydrocarbon as mentioned hereinbefore is characterized by markedly high rate of reaction, and has been employed for many years as a commercial process for the production of an aromatic carboxylic acid.

One of the problems with the above-mentioned process for producing an aromatic carboxylic acid consists in solid matters accompanying the oxidative reaction exhaust gas which is exhausted at the top of the reactor or in the vicinity thereof. The foregoing solid matters include not only fine solids of aromatic carboxylic acids, reaction byproducts and intermediate products each accompanying the oxidative reaction exhaust gas, but also aromatic carboxylic acids, reaction byproducts, intermediate products, catalytic components and the like each being dissolved in the droplets that are accompanied thereby.

The solid matters accompanying the oxidative reaction exhaust gas involve danger of adhering to walls of piping and inside walls of machinery and equipment on the downstream side of gas stream, and thereby impairing smooth running of reaction equipment. What is particularly problematic is the danger that the solid matters adhere to walls of a condenser which is placed immediately close to the downstream side of the reactor. When the solid matters, even if in a small amount, adhere to the walls of such a condenser, heat transfer is markedly inhibited, thus impairing the normal function of the condenser. If the worst case should happen, the gas stream itself is inhibited by blocking due to accumulated solid matters.

In such circumstances, various countermeasures thereaginst are proposed to suppress to the utmost, the foregoing solid matters accompanying the oxidative reaction exhaust gas. The proposals include, for instance, a method which comprises preserving a relatively large space above the liquid surface in a reactor, a method which comprises installing some shields or the like between vigorously bubbling liquid surface and a takeoff port of the oxidative reaction exhaust gas, a method which comprises imparting cleaning effect against solid matters by contriving and modifying the mechanism of returning to the reactor, acetic acid containing water as solvent that has been condensed, and the like methods.

Even if any or all the above-mentioned methods are devised, it is still impossible to perfectly eliminate the problematic solid matters accompanying the oxidative reaction exhaust gas.

SUMMARY OF THE INVENTION

It is a general object of the invention to provide a method for almost perfectly eliminate the occurrence of troubles and obstructions in a condenser which is caused by the solid matters accompanying the oxidative reaction exhaust gas in a process for producing an aromatic carboxylic acid by the oxidation of a poly-alkyl aromatic hydrocarbon.

Other objects of the invention will be obvious from the text of the specification hereinafter disclosed.

As a result of intensive research and investigation carried out by the present inventors, it has been found it possible to prevent the aforesaid troubles and obstructions in a condenser due to the solid matters accompanying the oxidative reaction exhaust gas by supplying part of a solvent to an inlet of oxidative reaction exhaust gas leading to a condenser. The present invention has been accomplished by the above-mentioned findings and information.

Specifically, the present invention provides a process for continuously producing an aromatic carboxylic acid which comprises (A) a step of subjecting a poly-alkyl aromatic hydrocarbon to a liquid-phase oxidation by continuously supplying an oxidation reactor with said hydrocarbon, a catalyst, a reaction accelerator, acetic acid containing water and a gas containing molecular oxygen gas;

(B) a step of continuously taking out from the oxidation reactor, the reaction products containing aromatic carboxylic acids, and separating the same into crude aromatic carboxylic acids and acetic acid containing water; and (C) a step of continuously taking out from the oxidation reactor, the oxidative reaction exhaust gas containing evaporated acetic acid containing water, introducing said gas in a condenser, and condensing the evaporated acetic acid containing water, wherein the step (C) further comprises supplying acetic acid containing water to an oxidative reaction exhaust gas inlet line leading to the condenser.

DESCRIPTION OF THE PREFERRED EMBODIMENTS

Figure 1:
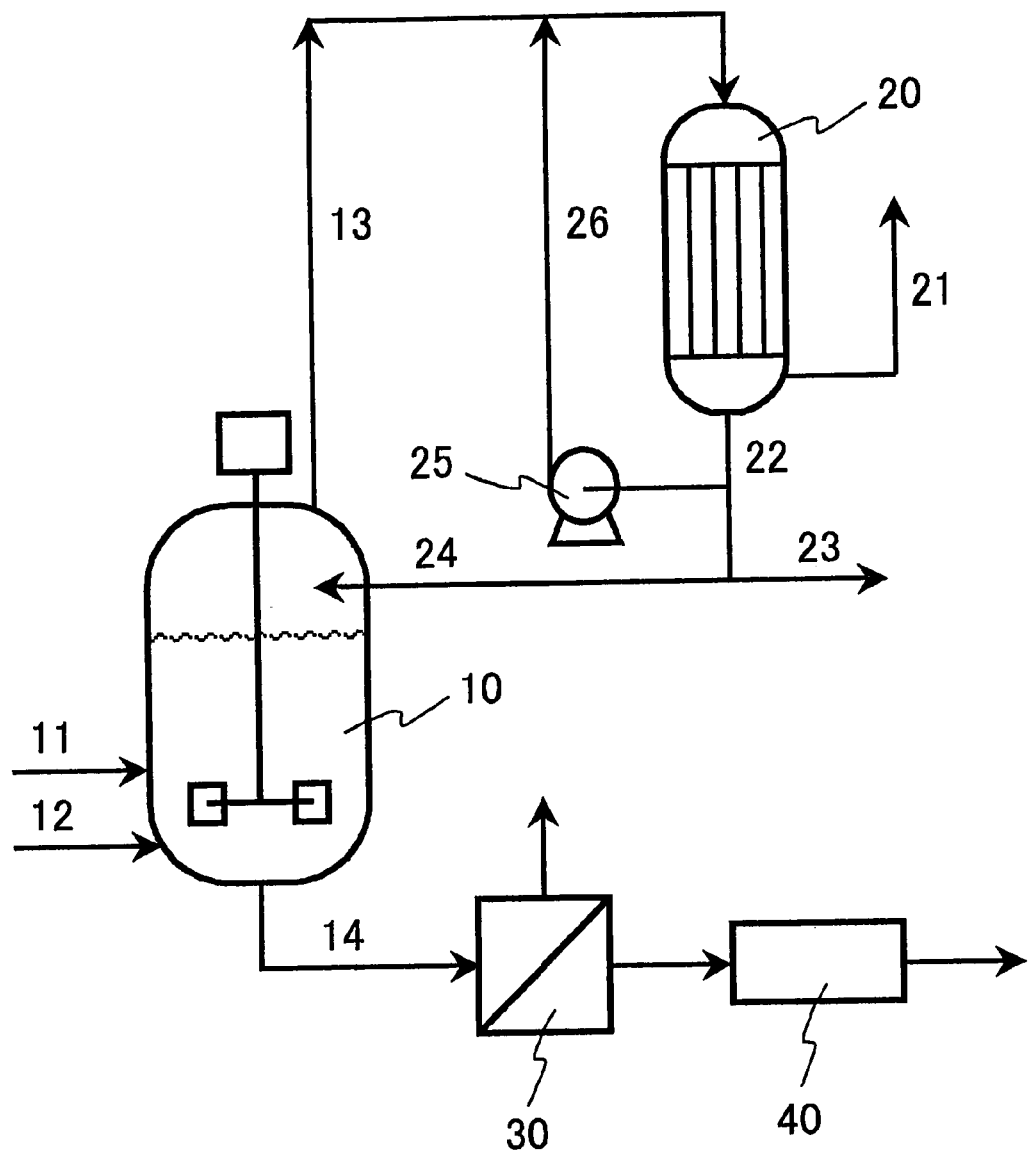
FIG. 1 is a schematic process flow diagram showing one example of process for producing an aromatic carboxylic acid according to the present invention, in which the symbols shall have the following designations:
10: oxidation reactor, 20: condenser, 30: separator, 40: dryer

Examples of poly-alkyl aromatic hydrocarbons that are used as a starting raw material in the process according to the present invention include di- and tri-alkylbenzenes such as o-xylene; m-xylene; p-xylene; trimethylbenzene; 2,6-dimethylnaphthalene; 2,7-dimethylnaphthalene; 2,6-diisopropylnaphthalene; and 4,4'-dimethylbiphenyl, poly-alkyl naphthalenes and poly-alkyl biphenyls.

Examples of aromatic carboxylic acids that are obtained by oxidizing the poly-alkyl aromatic hydrocarbons include orthophthalic acid, isophthalic acid, terephthalic acid, benzenetricarboxylic acid, 2,6-naphthalenedicarboxylic acid, 2,7-naphthalenedicarbo-xylic acid and 4,4'-biphenyldicarboxylic acid.

The process according to the present invention is optimally applicable to the production of isophthalic acid, terephthalic acid, trimellitic acid and naphthalenedicarboxylic acids among these aromatic carboxylic acids.

As a catalyst to be used for oxidative reaction, cobalt compounds and manganese compounds are usually employed. As a reaction accelerator, bromine compounds are generally employed.

The water content in the acetic acid containing water as solvent is usually 1 to 30% by weight, preferably 2 to 20% by weight.

In the process as illustrated in FIG. 1, a poly-alkyl aromatic hydrocarbon, a catalyst, a reaction accelerator and acetic acid containing water as solvent alone or as a mixture of optional two or more of the foregoing constitutional components are supplied to a oxidation reactor 10 through a line 11 or a plurality of lines. Pressurized gas containing molecular oxygen (usually air) is supplied to the oxidation reactor 10 through a line 12. The supply rate of air is controlled so that the oxygen concentration in the oxidative reaction exhaust gas which is exhausted through a line 13 is made to be at most 8% by volume on a solvent-free basis.

The reaction temperature in the oxidation reactor varies greatly depending upon the type of poly-alkyl aromatic hydrocarbon as a starting raw material and the selection of each of catalyst and reaction accelerator, and is in the range of 120 to 250° C. in a majority of cases. The pressure in the oxidation reactor at a prescribed reaction temperature needs only to be such a level as being capable of maintaining substantial liquid states of the starting raw material and the acetic acid containing water as the solvent.

The oxidation reactor 10 is tank type or a column type vessel, and generally equipped with an agitator, which however is not always necessary. Inside the oxidation reactor 10, the poly-alkyl aromatic hydrocarbon is subjected to oxidative reaction by the gas containing molecular oxygen in the presence of the catalyst and reaction accelerator. The oxidative reaction is accompanied with a large exothermic amount.

The heat of reaction generated as a result of oxidative reaction is removed from the oxidation reactor 10 by the latent heat of vaporization due to the vaporization of part of acetic acid containing water. The resultant vapor along with a small amount of decomposed products and the like, which accompany the oxidative reaction exhaust gas, are exhausted at the top of the oxidation reactor 10 through the line 13, and are introduced to one or two or more condenser 20.

The condensate which has been cooled and condensed in the condenser 20 is composed principally of acetic acid containing water, part of which is exhausted to the outside of the reaction system through a line 23, and the remainder of which is returned to the oxidation reactor 10 through a line 24. Non-condensable components are exhausted to the outside of the reaction system through a line 21.

The keystone of the process according to the present invention resides in pouring acetic acid containing water in the inlet line of the oxidative reaction exhausted gas leading to the condenser 20. There is no limitation on chemical composition or properties of the acetic acid containing water to be poured. Hence, arbitrary acetic acid containing water is usable, whether being present inside or outside the reaction system. However, the best means is, as illustrated on FIG. 1, a method in which the condensate obtained by condensation in the condenser 20 is poured with a pump 25. The condensate, although being withdrawn by branching midway from a line 22 on FIG. 1, can be withdrawn by branching midway from the line 23 or 24.

In the process on FIG. 1, the acetic acid containing water is poured substantially in the inlet line of the oxidative reaction exhausted gas leading to the condenser 20 by connecting a line 26 out of the delivery of the pump 25 to the line 13, but it goes without saying that the condensate may be directly poured in the condenser 20 without being limited to the process flow on FIG. 1.

The acetic acid containing water that is to be poured in the condenser 20, even if small in amount, exhibits its working effect. Usually, suitable amount thereof is 10 to 5000 parts by weight on the basis of 10000 parts by weight of crude aromatic carboxylic acid.

The process according to the present invention makes it possible to almost perfectly eliminate the occurrence of troubles and obstructions in a condenser which is caused by the solid matters accompanying the oxidative reaction exhaust gas by pouring acetic acid containing water in the inlet line of the condenser 20.

The stream containing the aromatic carboxylic acid formed by the oxidative reaction in the reactor is taken out through a line 14, is subjected to an additional oxidation step and a cooling crystallization step when necessary, and is introduced to a separator 30. In the separator 30, crystalline aromatic carboxylic acid is separated from mother liquor, and is sent to a dryer 40, where it is made into crude aromatic carboxylic acid as the objective product.

Part of the mother liquor which has been separated in the separator 30 is exhausted to the outside of the reaction system, and the remainder is recycled through the oxidation reactor 10.

In summarizing the working effect and advantage of the process according to the present invention for producing an aromatic carboxylic acid by oxidizing a poly-alkyl aromatic hydrocarbon, it is made possible to almost perfectly eliminate the occurrence of troubles and obstructions in a condenser which is caused by solid matters accompanying the oxidative reaction exhaust gas, and thus to proceed with stable operation by supplying acetic acid containing water in the inlet line of the condenser which allows the oxidative reaction exhaust gas to pass therethrough.

In the following, the present invention will be described in more detail with reference to working example and comparative example, which however shall not limit the present invention thereto.

The following example and comparative example were put into practice according to the schematic process flow diagram as illustrated in FIG. 1, wherein the oxidation reactor 10 was tank type and equipped inside with an agitating apparatus, and the condenser 20 was shell and tube type heat exchanger in which oxidative reaction exhaust gas comprising acetic acid containing water passed through the tube side.

The amount of each of the components in the examples and comparative examples was expressed by part or parts by weight required to produce 10000 parts by weight of crude terephthalic acid.

EXAMPLE 1

The oxidation reactor 10 was charged with the mixture as the starting material comprising 22000 parts by weight of acetic acid containing water (water content of 10% by weight) in which were dissolved as catalyst, 9.1 parts of Co, 5.6 parts of Mn and 15 parts of Br, and 6500 parts of p-xylene through the line 11, and with 31000 parts of air through the line 12. The inside of the reactor was vigorously agitated by the working effect of the agitator and the flow of air so as to proceed with oxidative reaction at a reaction temperature set to 190° C. The oxidative reaction product was taken out through the line 14 which product was in the form of slurry solution and contained about 30% by weight of terephthalic acid in the acetic acid containing water. The slurry solution was sent to the separator 30, where it was separated into the acetic acid containing water and wet crystal. The resultant wet crystal was dried in the dryer 40 to produce 10000 parts of crude terephthalic acid as the objective product.

The oxidative reaction exhaust gas accompanied with a large amount of vaporized acetic acid containing water was exhausted to the line 13 through the top of the oxidation reactor 10. The mixed vapor of acetic acid and water was condensed in the condenser 20, and was taken out through the line 22 as acetic acid containing water. At the same time, part of the resultant acetic acid containing water was taken out through the line 23 to the outside of the reaction system, and the remainder was returned to the oxidation reactor 10 through the line 24.

In addition, 500 parts out of the condensate (acetic acid containing water) in the condenser 20 was supplied midway in the line 13 through the line branched midway from the line 24 by means of the pump 25.

Continuous production of terephthalic acid was carried out for a period of about 5 months, while pouring the acetic acid containing water in the inlet line of the oxidative reaction exhaust gas leading to the condenser 20 in the above-mentioned manner.

After the completion of running, the condenser 20 was overhauled to inspect for solid matters. As a result, adhesion or accumulation of solid matters was hardly recognized.

Comparative Example 1

Terephthalic acid was continuously produced by oxidizing p-xylene in the same manner as in Example 1 except that the condensate was not poured in the inlet line of the oxidative reaction exhaust gas leading to the condenser 20. Specifically, the oxidation reactor 10 was charged with the mixture as the starting material comprising 22000 parts by weight of acetic acid containing water (water content of 10% by weight) in which were dissolved as catalyst, 9.1 parts of Co, 5.6 parts of Mn and 15 parts of Br, and 6500 parts of p-xylene through the line 11, and with 31000 parts of air through the line 12. The inside of the reactor was vigorously agitated by the working effect of the agitator and the flow of air so as to proceed with oxidative reaction at a reaction temperature set to 190° C. The oxidative reaction product was taken out through the line 14 which product was in the form of slurry solution and contained about 30% by weight of terephthalic acid in the acetic acid containing water. The slurry solution was sent to the separator 30, where it was separated into the acetic acid containing water and wet crystal. The resultant wet crystal was dried in the dryer 40 to produce 10000 parts of crude terephthalic acid as the objective product.

The oxidative reaction exhaust gas accompanied with a large amount of vaporized acetic acid containing water was exhausted to the line 13 through the top of the oxidation reactor 10. The mixed vapor of acetic acid and water was condensed in the condenser 20, and was taken out through the line 22 as acetic acid containing water. At the same time, part of the resultant acetic acid containing water was taken out through the line 23 to the outside of the reaction system, and the remainder was returned to the oxidation reactor 10 through the line 24.

Continuous production of terephthalic acid was carried out for a period of about 5 months without the use of the pump 25 and the line 26. After the completion of running, the condenser 20 was overhauled to inspect for solid matters. As a result, a large amount of solid matters adhered and accumulated in the inlet side of the oxidative reaction exhaust gas, and about 30% of the tubes were clogged up.

What is claimed is:

1. A process for continuously producing an aromatic carboxylic acid which comprises;
   (A) a step of subjecting a poly-alkyl aromatic hydrocarbon to a liquid-phase oxidation by continuously supplying an oxidation reactor with said hydrocarbon, a catalyst, a reaction accelerator, acetic acid containing water and a gas containing molecular oxygen gas;
   (B) a step of continuously taking out from the oxidation reactor, the reaction products containing aromatic carboxylic acids, and separating the same into crude aromatic carboxylic acids and acetic acid containing water; and (C) a step of continuously taking out from the oxidation reactor, the oxidative reaction exhaust gas containing evaporated acetic acid containing water, introducing said gas in a condenser, and condensing the evaporated acetic acid containing water, wherein the step (C) further comprises supplying condensed acetic acid containing water to an oxidative reaction exhaust gas inlet line leading to the condenser.

2. The process for continuously producing an aromatic carboxylic acid according to claim 1, wherein the condensed acetic acid containing water to be supplied to the oxidative reaction exhaust gas inlet line leading to the condenser is acetic acid containing water which is condensed in the condenser.

3. The process for continuously producing an aromatic carboxylic acid according to claim 1, wherein the amount of the condensed acetic acid containing water to be supplied to the oxidative reaction exhaust gas inlet line leading to the condenser is in the range of 10 to 5000 parts by weight based on 10000 parts by weight of crude aromatic carboxylic acid.

4. The process for continuously producing an aromatic carboxylic acid according to claim 1, wherein the poly-alkyl aromatic hydrocarbon is p-xylene and the aromatic carboxylic acid is terephthalic acid.

5. The process for continuingly producing an aromatic carboxylic acid according to claim 1, wherein said condensed acetic acid containing water is liquid acetic acid containing water.

6. The process for continuously producing an aromatic carboxylic acid according to claim 5, wherein said liquid acetic acid containing water is supplied to said oxidative reaction exhaust gas inlet line so as to clean said oxidative reaction exhaust gas inlet line and said condenser.

7. The process for continuously producing an aromatic carboxylic acid according to claim 6, wherein an amount of the liquid acetic acid containing water supplied to the oxidative reaction exhaust gas inlet line is 10 to 5000 parts by weight based on 10000 parts by weight of crude aromatic carboxylic acid.

8. The process for continuously producing an aromatic carboxylic acid according to claim 1, wherein said condensed acetic acid containing water is supplied to said oxidative reaction exhaust gas inlet line so as to clean said oxidative reaction exhaust gas inlet line and said condenser.

9. In a process for continuously producing an aromatic carboxylic acid comprising:

(A) a step of subjecting a poly-alkyl aromatic hydrocarbon to a liquid-phase oxidation by continuously supplying an oxidation reactor with said hydrocarbon, a catalyst, a reaction accelerator, acetic acid containing water and a gas containing molecular oxygen gas;

(B) a step of continuously taking out from the oxidation reactor, the reaction products containing aromatic carboxylic acids, and separating the same into crude aromatic carboxylic acids and acetic acid containing water; and (C) a step of continuously taking out from the oxidation reactor, the oxidative reaction exhaust gas containing evaporated acetic acid containing water, introducing said gas in a condenser, and condensing the evaporated acetic acid containing water, wherein the improvement comprises, in said step (C), supplying acetic acid containing water, additional to said evaporated acetic acid containing water, to an oxidative reaction exhaust gas inlet line leading to the condenser.

10. The process for continuously producing an aromatic carboxylic acid according to claim 9, wherein said acetic acid containing water, additional to said evaporated acetic acid containing water, is condensed acetic acid containing water.

11. The process for continuously producing an aromatic carboxylic acid according to claim 10, wherein said condensed acetic acid containing water is acetic acid containing water which has been condensed in said condenser.

12. The process for continuously producing an aromatic carboxylic acid according to claim 9, wherein said acetic acid containing water, additional to said evaporated acetic acid containing water, is liquid acetic acid containing water.

13. The process for continuously producing an aromatic carboxylic acid according to claim 9, wherein said acetic acid containing water, additional to said evaporated acetic acid containing water, is supplied to said oxidative reaction exhaust gas inlet line so as to clean said oxidative reaction exhaust gas inlet line and said condenser.

14. The process for continuously producing an aromatic carboxylic acid according to claim 9, wherein said acetic acid containing water, additional to said evaporated acetic acid containing water, is supplied to the oxidative reaction exhaust gas inlet line downstream from said oxidation reactor and upstream of said condenser.

* * * * *